United States Patent [19]
Kelman

[11] Patent Number: 5,596,378
[45] Date of Patent: Jan. 21, 1997

[54] LENS SELECTION SYSTEM

[76] Inventor: Charles D. Kelman, 721 Fifth Ave., New York, N.Y. 10022

[21] Appl. No.: 563,744

[22] Filed: Nov. 29, 1995

Related U.S. Application Data

[63] Continuation of Ser. No. 180,561, Jan. 12, 1994, abandoned.

[51] Int. Cl.$^6$ .................................. A61B 3/02; A61B 3/00
[52] U.S. Cl. ..................... 351/233; 351/222; 351/246
[58] Field of Search .................................. 351/222, 223, 351/233, 234, 239, 244, 245, 246

[56] References Cited

U.S. PATENT DOCUMENTS

| | | | |
|---|---|---|---|
| 763,929 | 6/1904 | Reinhard et al. | 351/234 |
| 4,413,891 | 11/1983 | Rybicki | 351/235 |
| 4,798,457 | 1/1989 | Morohashi et al. | 351/234 X |
| 5,220,362 | 6/1993 | Blenkle | 351/235 |
| 5,285,224 | 2/1994 | Sims | 351/233 X |

*Primary Examiner*—Hung X. Dang
*Attorney, Agent, or Firm*—Darby & Darby

[57] ABSTRACT

An eyeglass lens selection system for untrained persons includes a carrier that is slidably mounted in a viewer module. An eye chart faces the viewer module and an elongated arm connects the chart to the viewer module and lens carrier. The carrier is an elongated strip having a plurality of lenses along its length, each of the lenses has a different refractive power. The lenses are molded of polymethyl methacrylate in a one-piece lens/carrier assembly. In use, a prospective purchaser of eyeglasses looks with one eye at the eye chart through an opening in the viewer module and through a single lens on the carrier. The carrier is slidingly moved through the viewer module so that each lens, in turn, is used in viewing the eye chart until a clear image on the chart is obtained. The procedure is repeated for the other eye. The lenses that provide the clear images are identified from indicia on the carrier and eyeglasses are assembled from kits containing a large number of lenses in different optical strengths, and a selection of eyeglass frames that can accommodate the selected lenses.

21 Claims, 3 Drawing Sheets

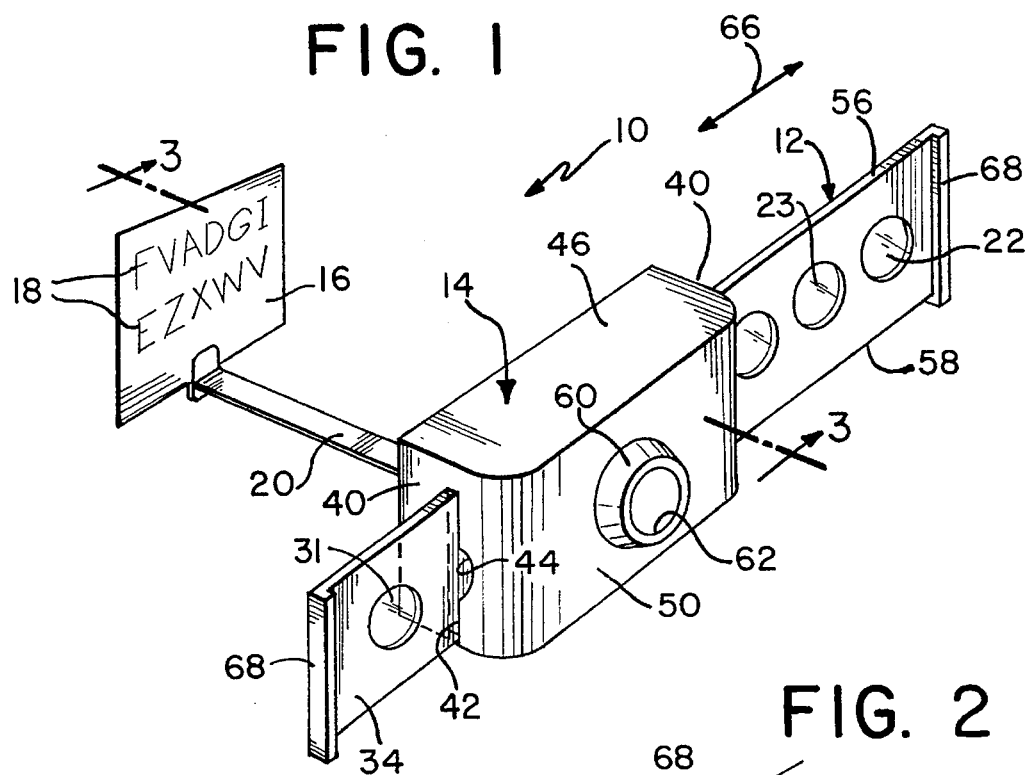
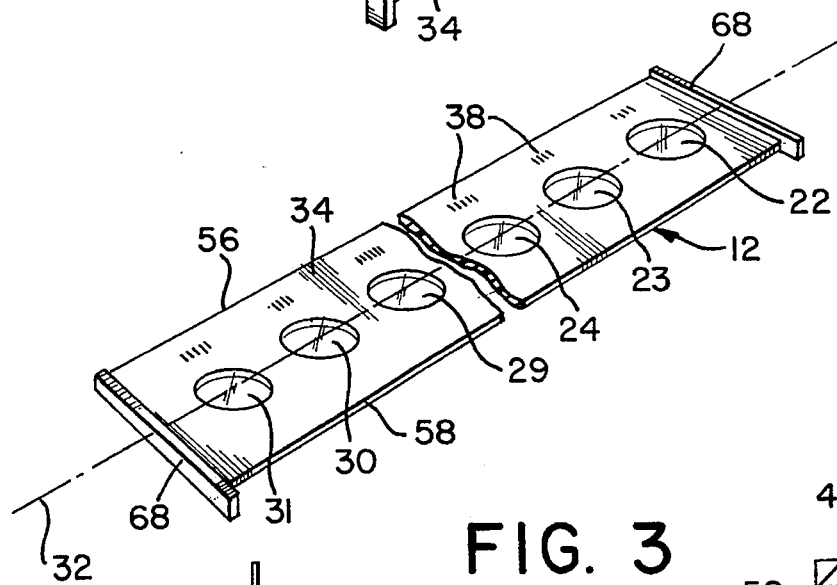
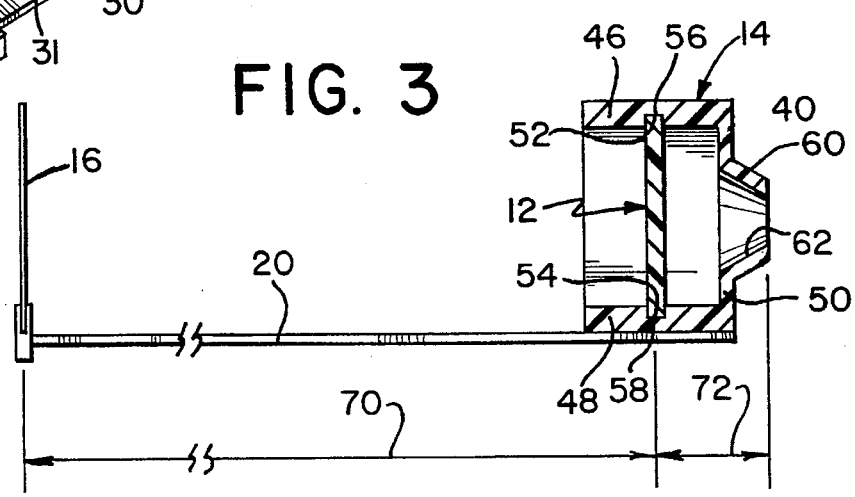

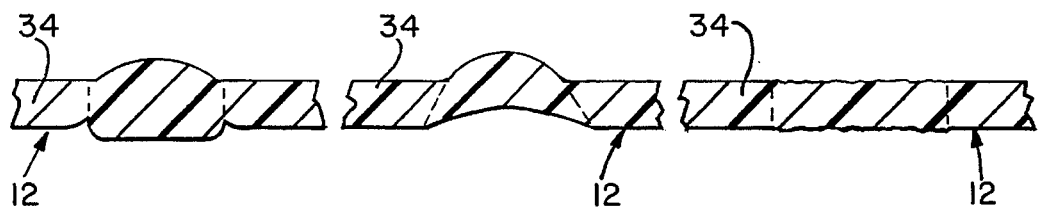
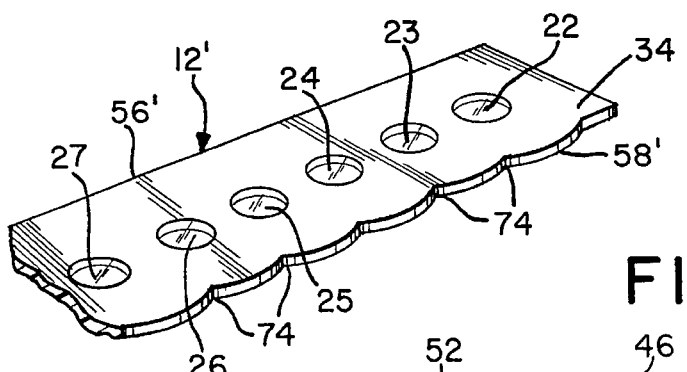
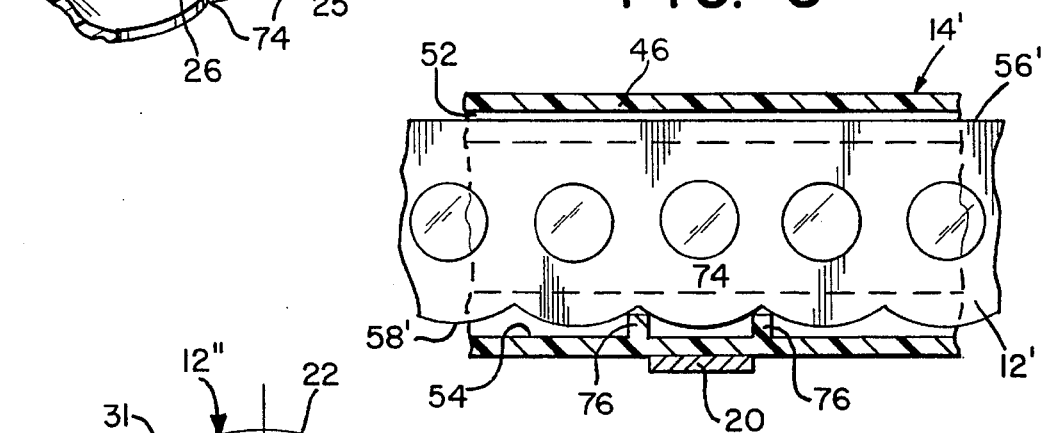
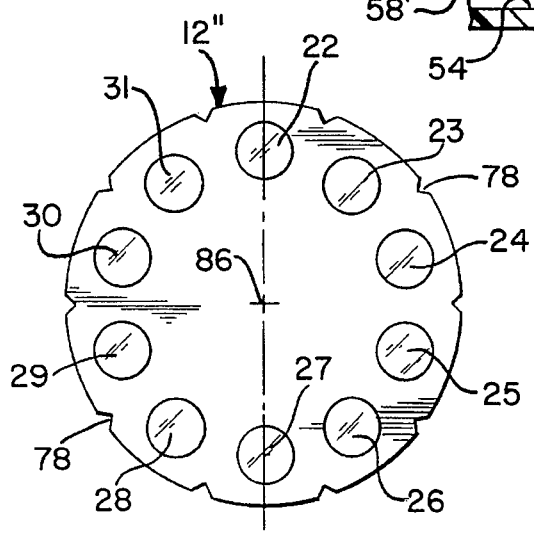

LENS SELECTION SYSTEM

This is a continuation of application Ser. No. 08/180,561, filed Jan. 12, 1994 now abandoned.

BACKGROUND OF THE INVENTION

This invention relates generally to a method and apparatus for correcting human vision problems by means of eyeglasses and more particularly to a method and apparatus that allow an untrained individual to select eyeglass lenses to correct the individual's personal vision problems.

Large numbers of people overcome simple vision problems by selecting ready-made eyeglasses that are available in racks in supermarkets, drugstores, and the like. The glasses, generally for reading purposes, are available in a range of lens power so that a person can try on one pair of glasses after another. In many instances, a satisfactory pair is found, that is, the person is able to read printed matter that previously he or she was unable to read, or only with difficulty because the images were blurred.

In this way, many people resolve a vision problem at a substantially reduced cost as compared with visits to an ophthalmologist or optometrist and subsequently an optician. The latter procedure would provide an eye examination, a lens prescription and ultimately fitting of eyeglasses. Whereas the variety of styles in lens frames that is available through such conventional channels is substantial, the cost exceeds the do-it-yourself, trial-and-error procedure for selecting simple glasses.

More complex vision problems, for example, those where astigmatism is present, are not readily resolved by eyeglasses that may be tried on at the drugstore rack. Particularly, the ready-to-wear eyeglasses that are found in drugstores and the like have the same corrective lenses for both eyes. In such a situation, where the lens requirement for each eye is different, the more costly route must be followed as ready-to-wear glasses are not available with different lens powers for each eye.

What is needed is a system whereby the untrained person can readily determine his or her corrective needs for each eye individually, and can translate that information into a pair of eyeglasses that can be quickly and easily assembled with a different lens on each side to accommodate the individual's vision requirements.

SUMMARY OF THE INVENTION

It is an object of the invention to provide an improved lens selection system that allows an untrained person to select lenses for a pair of eyeglasses, even when vision in the eyes is unequal.

It is another object of the invention to provide an improved lens selection system whereby standardized lenses and frame components may be assembled into a wide variety of completed eyeglasses, customized to an individual's vision needs.

Yet another object of the invention is to provide an improved lens selection system that provides a low cost solution to the problem of providing eyeglasses, wherein the right and left lenses are of unequal power.

A lens selection system in accordance with the invention includes a carrier that is slidably mounted in a viewer module. An eye chart having indicia on its surface facing the viewer module is connected to the viewer module and lens carrier by means of an elongated arm.

The carrier is preferably an elongated strip which comprises a plurality of lenses along the length thereof, each of the lenses has a different refractive power or strength. The lenses are preferably arranged along the length of the carrier in fixed positions. The power of each lens preferably increases in increments of ¼ diopter from lens-to-lens on the carrier, which is preferably made of polymethyl methacrylate (PMMA) having a high optical clarity permitting 92% light transmission. The lenses are preferably molded in the carrier in the form of a one piece lens/carrier assembly. Thus, no additional operations are required in preparing or mounting the lenses to the carrier. The carrier includes identifying indicia for each lens.

In use, a prospective purchaser of eyeglasses looks at the eye chart through an opening in the viewer module and through a single lens on the carrier. The carrier is slidingly moved through the viewer module so that each lens on the carrier, in turn, is used in viewing the eye chart until a clear image on the chart is obtained. The lens on the carrier that provides the clear image is identified from the indicia on the carrier and eyeglasses are assembled from kits. A large plurality of lenses in different optical strengths corresponding to the lenses on the carrier and a selection of eyeglass frames that can accommodate the selected lenses, are provided in the kits.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description of preferred embodiments, taken in connection with the accompanying drawings, in which:

FIG. 1 is a top perspective view of a lens selection system in accordance with the invention;

FIG. 2 is a front perspective view of a rectilinear carrier for use in the system of FIG. 1;

FIG. 3 is a sectional view in elevation taken along the line 3—3 of FIG. 1;

FIGS. 4a–c are partial top sectional views of the carrier of FIG. 2;

FIG. 5 is a front perspective view of an alternative embodiment in accordance with the invention of a carrier similar to that in FIG. 2;

FIG. 6 is a partial sectional view in elevation of the carrier of FIG. 5 in a lens selection system in accordance with the invention;

FIG. 7 is a front elevation view of an alternative carrier in accordance with the invention;

DESCRIPTION OF THE PREFERRED EMBODIMENTS

Figure 8:
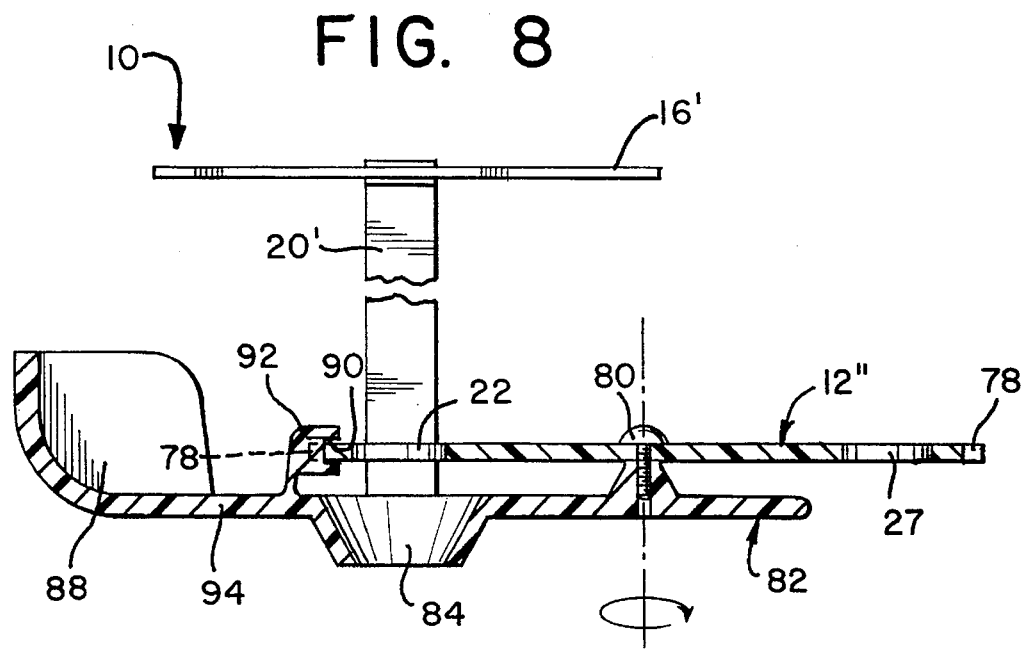
FIG. 8 is a sectional top view of an alternative embodiment of a lens selection system in accordance with the invention using the carrier of FIG. 7.
Figure 9A:
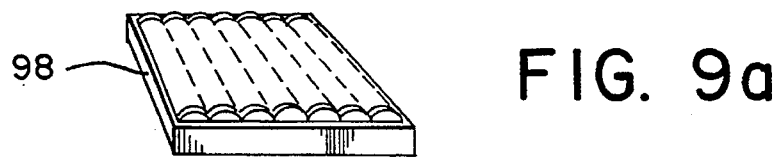
FIGS. 9a, b are lens and frame kits, respectively, in accordance with the invention.
Figure 9B:
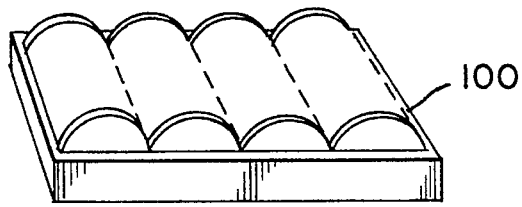

With reference to FIGS. 1–4, a lens selection system 10 includes a lens carrier 12 that is slidably mounted in a viewer module or carrier holder 14. An eye chart 16 having indicia 18 on a surface thereof facing the viewer module 14, is connected to the viewer module 14 and lens carrier 12 by means of an elongated arm 20.

The carrier 12 includes a plurality of lenses 22–31, each of a different refractive power or strength and arranged along the length of the carrier 12 with the center of each lens 22–31 lying on a common line 32. Ten lenses test 22–31 are illustrated although the number of lenses is not so limited. The power of each lens increases in increments from lens to lens, for example, in increments of ¼ diopter. Thus, in the lens carrier 12 of FIG. 2, the range in diopters may extend from 1 diopter in lens 22 through 3¼ diopters in lens 31. The diameter of each lens may be approximately 1 inch.

The lens carrier 12 is made of polymethyl methacrylate, an acrylic resin having high optical clarity which permits 92% light transmission. This plastic material can be molded by many techniques and the resultant product has excellent weathering resistance, good impact strength and is odorless and non-toxic, even when burning.

The test lenses 22–31 are molded as one piece with the planar portion 34. Thus, the optical lens contours are molded when the entire carrier 12 is molded. Thus, no additional operations are required in preparing or mounting the lenses to the plate portion 34. However, assembly of a carrier by attaching individual lenses to a planar sheet having suitable apertures is not precluded from the scope of the invention.

As illustrated in FIGS. 4a–c, the test lenses may be convex or concave relative to the planar portion 34 on one or both opposed faces of the carrier 12, or the entire lens may be generally flush with the opposed planar faces as is the case with a Fresnel lens illustrated in FIG. 4c.

Carriers may have, as stated, different quantities of lenses, and the incremental differences in optical power may differ from that discussed above. Also, carriers may be prepared to satisfy the specific needs of different age groups wherein known differences in corrective requirements exist.

The carrier includes identifying indicia 36 that is marked on the planar portion 34, and each test lens is identified on the planar portion 34 with indicia 38 that identifies the optical power of the respective lens, for example, in diopters. On the other hand, the lens indicia 38 may merely state a consecutive number, symbol, or character to identify the respective lenses. As explained more fully hereinafter, it is not necessary that the untrained person who uses the lens selection system 10 in accordance with the invention, be knowledgeable with respect to the exact refractive power of the lenses.

The viewer module or carrier holder 14 provides a support structure for the lens carrier 12 and includes a pair of similar end walls 40, each of which has a vertical slot 42 through which the lens carrier 12 is slidingly positioned. A cut out portion 44 is provided on the vertical edges of the slots 42 to accommodate convex lenses that bulge, such as illustrated in FIG. 4a.

The viewer module 14 also includes a top wall 46 and a bottom wall 48 that join integrally to the end 40 and to a rear panel 50. Grooves 52, 54, in the top wall 46 and bottom wall 48 of the viewer module 14 provide tracks for the upper and lower edges 56, 58 of the carrier 12. A boss 60 extends from the rear panel 50 and has an opening 62 that is positioned between the top 46 and bottom 48 of the viewer module 14 such that when the lens carrier 12 is mounted in the slots 42, the centers of the lenses, that is, the line 32, is centered relative to the opening 62.

The front of the viewer module 14, that is, the side opposite to the rear panel 50 is at least partly open.

The elongate arm 20 connects to the bottom 48 of the viewer module 14 and extends at right angles to the plane of the lens carrier 12. An eye chart 16 is connected to the arm 20 and has indicia 18 that are suitable for use in determining the degree of correction needed to compensate for deficiencies in a person's vision. The eye chart may be of the conventional type well-known for use in eye examinations by doctors and optometrists. The eye chart 16 preferably is positioned at a right angle to the elongate arm 20, with the center of the chart in substantial alignment with the line of sight viewing the chart 16 through the opening 62 and through an aligned lens on the lens carrier 12.

The lens carrier 12 can be slid back and forth in the slots 42 as indicated by the double headed arrow 66. Depending stops 68 that extend below the lower edge 58 of the carrier 12 impede any slide-through of the carrier 12 that would separate the carrier from the carrier holder or viewer module 14. The stops 68 can be connected to the carrier 12 after the carrier is slipped through the slots 42, or the stop 68 can be molded as a permanent part of the carrier 12 when top clearance is provided between the upper edge 56 of the carrier 12 and the groove 52 in the top 46 of the viewer module 14.

The lens selection system 10 in accordance with the invention is used in conjunction with a supply of eyeglass lenses in an assortment or kit 98 that includes all of the lens strengths that are present in the lenses 22–31 on the lens carrier 12. Additionally, a supply or kit 100 of eyeglass lens frames without lenses is furnished. The aforementioned eyeglass lenses are preferably shaped, and the lens frames are preferably configured such that any lens regardless of power can be snapped into any selected lens frame. The lenses however may come in an assortment of shapes and sizes, as will the lens frames, so that style preferences may be accommodated and a comfortable physical fit may be achieved as well as a suitable optical "fit".

The individual eyeglass lenses in the kit 98 are identified by their wrappings or a label with the diopter power, or by a marking that corresponds with the indicia 38 adjacent each of the respective lenses on the lens carrier 12.

In using the lens selection system 10, a prospective purchaser of eyeglasses looks with one eye through the opening 62 in the viewer module 14 at the eye chart 16, positioning in turn each of the lenses 22–31 in alignment with the opening 62, until the desired line of indicia on the eye chart is seen clearly. At that time, the person notes the indicia 38 that is associated with the lens on the carrier 12 that provides the best vision.

This procedure is followed for each eye so that the corrective lens that is required for each eye, respectively, is determined, even though different levels of lens power are required for each eye.

Then, the person selects a frame size from the frame kit 100 for comfort or appearance and selects a right and a left eye lens in accordance with the earlier determination that was made using the carrier 12. The selected eyeglass lenses are then snapped into the eyeglass frames to complete the eyeglasses.

Figure 10:
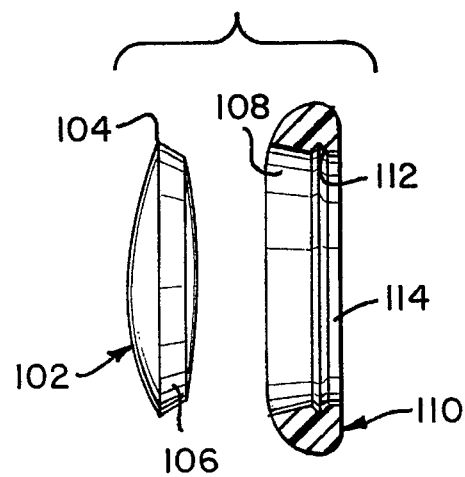
FIG. 10 is a side sectional view of a lens positioned for insertion in an eyeglass frame.

As illustrated in FIG. 10, the eyeglass lens 102 from the kit 98 has a protruding peripheral edge 104 and bevelled surface 106 that enables the lens 102 to be pressed along a tapered surface 108 of a slightly flexible eyeglass frame 110, from the kit 100, until the edge 104 engages an inner groove 112 around the lens opening 114 of the eyeglass frame 110.

This procedure is completed by an untrained person who follows instructions that are provided in the shop or store where the lens selection system 10 is provided together with the lens and frame kits. On the other hand, after the purchaser has selected a pair of lenses using the system 10, the eyeglasses may be assembled by a store attendant.

The distance between the eye chart 16 and the lens on the lens carrier 12, and the distance 72 between the opening 62 and the carrier 12 are preset to correspond to normal reading distances from the eyes of a person wearing glasses.

FIG. 5 illustrates an alternative embodiment of a lens carrier 12' in accordance with the invention. The carrier 12' is similar to the carrier 12 of FIG. 2 with the exception of the lower edge 58' which is gently scalloped so as to provide a series of depressions 74 that have the same spacings as the center spacings of the lenses 22–31 from each adjacent lens. That is, the lenses and the depressions 74 have the same pitch.

A pair of rounded projections 76 extend upwardly from the base of the groove 54 in a viewer module 14'. The projections 76 are spaced apart by the pitch distance of the lenses 22–31 such that when the carrier 12' is slid through the slots 42 in the viewer module 14', there are inherent stop positions in which the carrier 12' will tend to come to rest with the respective lens in the carrier 12' in accurate alignment with the center of the opening 62 in the viewer module 14', and in alignment with the center of the eye chart 18. Thus, ease in using the lens selection system 10 is enhanced, as is the accuracy of the results when proper alignment between the user's eye, the lens and the chart is assured.

It will be readily apparent that other patterns for the lenses 22–31, other than a linear arrangement, can be provided with a suitable complementary configuration of a carrier holder or viewer module. FIG. 7 illustrates a lens carrier 12" wherein the lenses 22–31 are mounted on a plate around a common circle and equally spaced one from the other. A plurality of notches 78 are formed into the circular periphery of the carrier 12", the peripheral angular spacing of these notches corresponding to the angular spacing between the respective lenses.

The circular carrier 12" is rotatably connected under a screw head 80, to a viewer module 82 having an opening 84 that is in alignment with the lenses 22–31 on the carrier 12' as that plate is rotated about the axis 86. An arm 20', similar to the arm 20 of FIG. 1, extends to an eye chart 16'. The arm 20' is in alignment with the opening 84 and a positioned lens on the circular carrier 12". A handle 88 of the viewer module 82 enables a user to grip the viewer module 82 with one hand and rotate the lens carrier 12" with the other hand so as to look at the eye chart through each lens, in turn, by way of the opening 84.

A groove 90 is provided on a resilient finger 92 that extends from the main portion 94 of the viewer module 82. An inner edge of the groove 90 engages the notches 78 on the outer periphery of the circular lens carrier 12" as the plate 12" is rotated to provide natural stops where the lens on the disk 12" is in accurate alignment with the opening 84 on the viewer module 82. Thereby, the best selection of lenses is facilitated.

In another alternative embodiment (not shown) in accordance with the invention, the lenses 22–31 may be formed integrally in or mounted to a flexible material that is provided on a roll or in the form of an endless belt so that the lenses can, in turn, be reeled past an opening for viewing the eye chart therethrough.

As stated, in every embodiment, the would-be purchaser of eyeglasses views the reading chart through the viewer module opening and through the available lenses on the carrier device, in turn, until the best lens is selected. Then, eyeglass lenses of the selected powers are taken from the available supply and a frame is selected from the available frames, and a complete set of eyeglasses is assembled in a very short time. A different lens power may be selected, as suits the user's vision needs, for each side of the finished eyeglasses.

It will thus be seen that the objects set forth above, among those made apparent from the preceding description, are efficiently attained and, since certain changes may be made in carrying out the above method and the in the constructions set forth without departing from the spirit and scope of the invention, it is intended that all matter contained in the above description and shown in the accompanying drawings shall be interpreted as illustrative and not in a limiting sense.

What is claimed is:

1. An eyeglass lens selection system for permitting a consumer to separately select desired individual lenses for a pair of eyeglasses without assistance, said system comprising:

at least one carrier for holding a plurality of lenses in a substantially coplanar and fixed relationship relative to each other, at least one of said lenses being of a different optical power from another of said lenses, wherein:

said carrier has a front face and a rear face; individual single lenses of said plurality of lenses are generally in a plane of said carrier defined by said faces;

said lenses permit light to pass through said carrier;

said carrier includes individual identifying indicia associated with each said individual single lens; and said individual indicia associated with each individual single lens corresponds to individual identifying indicia associated with an individual eyeglass lens for placing into eyeglass frames to form a pair of eyeglasses such that reference to only a single carrier is necessary for selecting an eyeglass lens;

said system further comprising a viewer having a track for guiding a single carrier, said viewer accommodating only one carrier at a time so that a consumer slides only a single carrier to position a single lens in front of one eye at a time to select an appropriate eyeglass lens for each eye as determined without referring to any information other than said individual indicia associated with a single lens on said single carrier that provides the clearest vision for the consumer.

2. An eyeglass lens selection system as in claim 1, wherein said lenses are integral with said carrier.

3. An eyeglass lens selection system as in claim 1, wherein said carrier is generally rectilinear, said lenses having respective centers on a common line, said lenses by their respective optical powers providing a continuous range of powers in incremental steps on said carrier.

4. An eyeglass lens selection system as in claim 1, wherein said carrier is generally circular, said lenses being uniformly spaced from the circular center of said carrier, said lenses by their respective optical powers providing a continuous range of powers in incremental steps on said carrier.

5. An eyeglass lens selection system as in claim 1, wherein said further comprises an opening therethrough, said track of said viewer being at a fixed distance from said opening, each of said plurality of lenses being individually alignable with said opening by sliding of said single carrier along said track and relative to said viewer.

6. An eyeglass lens selection system as in claim 5, wherein said carrier is rectilinear and includes an upper edge and a lower edge, and said viewer includes an upper track and a lower track, said carrier being slidable in said upper and lower tracks to align said lenses individually with said opening.

7. An eyeglass lens selection system as in claim 5, further comprising eye chart means having indicia thereon and positioned parallel to said lens carrier, and means extending between said viewer and said chart means for fixing a selected distance between said chart means and said opening in said viewer.

8. An eyeglass lens selection system as in claim 5, further comprising engagement means on one of said carrier and said viewer and at least one protrusion on the other of said carrier and said viewer, interengagement of said engagement means and said at one least protrusion releasibly holding at least one of said lenses in alignment with said opening in said viewer.

9. An eyeglass lens selection system as in claim 8, wherein:
said carrier is rectilinear and includes an upper edge and a lower edge;
said viewer includes an upper track and a lower track for said upper edge and said lower edge, respectively, of said single carrier;
said carrier is slidable in upper and lower tracks to align said lenses individually with said opening;
said engagement means is at least one depression on one of said upper and lower edges of said carrier; and
said at least one protrusion extends from a surface of one of said upper and lower tracks.

10. An eyeglass lens selection system as in claim 8, wherein:
said carrier is circular;
said viewer includes a single track having a groove;
said carrier is slidable in said groove to align said lenses individually with said opening;
said engagement means is at least one peripheral depression on said edge of said carrier; and
said at least one protrusion extends from a surface of said groove.

11. An eyeglass lens selection system as in claim 5, wherein said carrier is generally circular and rotatably mounted at its center to said viewer to align said lenses in turn with said opening.

12. An eyeglass lens selection system as in claim 1, wherein said lenses differ from each other in increments of ¼ diopter.

13. An eyeglass lens selection system as in claim 12, wherein the quantity of said lenses is in a range of approximately six to fifteen.

14. An eyeglass lens selection system as in claim 1, wherein said individual identifying indicia on said single carrier each are correlated to the optical power of an associated lens on said single carrier and the corresponding eyeglass lens so that, upon selecting an appropriate lens that provides the clearest vision for the consumer, a corresponding eyeglass lens may be selected using only the single indicia identifying the selected individual desired lens from said single carrier, said system further including a plurality of carriers each holding a plurality of lenses, said lenses differing in optical power from carrier to carrier to provide a variety of lenses from which a consumer may select an appropriate lens, said viewer accommodating sequentially inserted single carriers of said plurality of carriers.

15. An eyeglass lens selection system as in claim 1 wherein said lenses are integrally molded with said carrier.

16. An eyeglass lens selection system as in claim 15 wherein said lenses and said carrier are one piece of polymethyl methacrylate.

17. An eyeglass lens selection system as in claim 1 wherein:
at least one of said lenses is a Fresnel lens;
said carrier has a front and a rear planar surface; and
at least one of said lenses is entirely between said planar surfaces thereof.

18. A method for selection and assembly of eyeglasses by a consumer without assistance, said method comprising the steps of:
a) providing in a shop or store an assortment of available individual eyeglass lenses having different optical powers and each having associated identifying indicia;
b) providing an assortment of eyeglass frames without lenses into which lenses from said assortment of individual eyeglass lenses may be fitted;
c) providing a lens carrier having a plurality of single test lenses individually arranged in a substantially coplanar and fixed relationship relative to each other, each said single test lens being of a different optical power, said carrier further comprising individual identifying indicia for each single test lens and corresponding to one of said plurality of eyeglass lenses;
d) providing a viewer with an opening therethrough, an eye chart arranged at a viewing distance from said opening, and a track for a single carrier positioned in front of said viewer opening such that only one carrier at a time may be positioned in front of said viewer opening;
e) positioning only a single carrier in said track of said viewer;
f) sliding said single carrier in said track to sequentially position, in turn, a single test lens in front of said viewer opening and with only one eye observing said eye chart through said opening and through a single positioned test lens until a clear reading on said eye chart is obtained;
g) identifying the single test lens on said single lens carrier that provides said clear reading by referring only to individual indicia provided on said single carrier adjacent said single lens;
h) repeating steps e and f except only for the other eye;
i) selecting a pair of eyeglass lenses within the shop or store from said plurality of available eyeglass lenses having identifying indicia by locating an eyeglass lens with identifying indicia that correspond to the indicia adjacent the single test lenses determined respectively for each eye in steps e through g;
j) selecting an eyeglass frame; and
k) inserting the selected eyeglass lenses in the selected eyeglass frame to complete a pair of eyeglasses;
wherein the consumer independently performs at least steps e through j without requiring assistance and without referring to any information other than individual indicia on a single carrier associated with a single lens and indicia on said available eyeglass lenses corresponding to said indicia on said single carrier.

19. A method as in claim 18, wherein step j includes pressing a bevelled surface of a selected one of the lenses along a tapered surface of a lens opening of the eyeglass frame until a protruding peripheral edge of the selected one of the lenses reaches an inner groove of said lens opening.

20. A method for selection and assembly of eyeglasses by a consumer without assistance, said method comprising the steps of:

a) observing with only one eye an eye chart through an opening in a viewer and through a positioned single one of a plurality of test lenses individually aligned on a single lens carrier until a clear reading on an eye chart is obtained, said eye chart being arranged at a viewing distance from said opening;

b) identifying which single test lens provides said clear reading by referring only to individual indicia on said single carrier adjacent said single test lens that provides said clear reading, said test lenses being individually arranged in a substantially coplanar and fixed relationship relative to each other, and being of different optical powers;

c) providing in a shop or store a plurality of available eyeglass lenses whose optical powers correspond to those of said single test lenses, said eyeglass lenses having associated indicia corresponding to said individual indicia on said carrier adjacent said single test lenses;

d) repeating steps a and b except only for the other eye;

e) selecting a pair of eyeglass lenses within the shop or store from said plurality of available eyeglass lenses that correspond to the single test lenses determined respectively for each eye in steps a and b by referring only to said individual indicia adjacent said single test lens that provides said clear reading and said indicia associated with said available eyeglass lenses;

f) providing an eyeglass frame; and g) inserting the selected eyeglass lenses in an eyeglass frame to complete a pair of eyeglasses;

wherein at least steps a, b, d, and e are performed independently by the consumer without requiring assistance and without referring to any information other than individual indicia on a single carrier associated with a single test lens and indicia associated with said available eyeglass lenses and corresponding to said indicia on said single carrier.

21. A method as in claim 20, wherein the eyeglass frame has a lens opening with a tapered surface and one of a protruding peripheral edge and an inner groove, said selected eyeglass lenses each having the other of a protruding peripheral edge and the inner groove, said selected eyeglass lenses each having a bevelled surface configured for pressing along said tapered surface until said peripheral edge engages said inner groove, step f including pressing the bevelled surface along the tapered surface until one of the protruding peripheral edge and inner groove of the selected eyeglass lenses reaches the other of the protruding peripheral edge and the inner groove of said lens opening.

* * * * *